United States Patent [19]
Washburn et al.

[11] Patent Number: 6,071,241
[45] Date of Patent: Jun. 6, 2000

[54] ULTRASOUND COLOR FLOW DISPLAY OPTIMIZATION BY ADJUSTMENT OF THRESHOLD USING SAMPLING

[75] Inventors: Michael J. Washburn, New Berlin; Gary E. MacLeod, Menomonle Falls; Sean D. Lucas, Waukbha; David J. Muzilla, Muknonago, all of Wis.

[73] Assignee: General Electric Company, Milwaukee, Wis.

[21] Appl. No.: 09/223,990

[22] Filed: Dec. 31, 1998

[51] Int. Cl.[7] .................................................. A61B 8/02
[52] U.S. Cl. ........................................... 600/454; 600/455
[58] Field of Search .................................. 600/441, 443, 600/447, 454, 453, 458

[56] References Cited

U.S. PATENT DOCUMENTS

| | | | |
|---|---|---|---|
| 5,349,524 | 9/1994 | Daft et al. | 600/441 |
| 5,735,797 | 4/1998 | Muzilla et al. | 600/441 |
| 5,865,750 | 2/1999 | Hatfield et al. | 600/443 |
| 5,897,502 | 4/1999 | Wong et al. | 600/454 |
| 5,908,391 | 6/1999 | Muzilla et al. | 600/454 |
| 6,017,309 | 1/2000 | Washburn et al. | 600/454 |

*Primary Examiner*—Marvin M. Lateef
*Assistant Examiner*—Ali M. Imam
*Attorney, Agent, or Firm*—Ronald E. Larson; Christian G. Cabou; Phyllis Y. Price

[57] ABSTRACT

An ultrasound color flow imaging system is programmed to optimize display images of power and velocity by automatically adjusting thresholds by using histograms and samplings of color flow data.

22 Claims, 2 Drawing Sheets

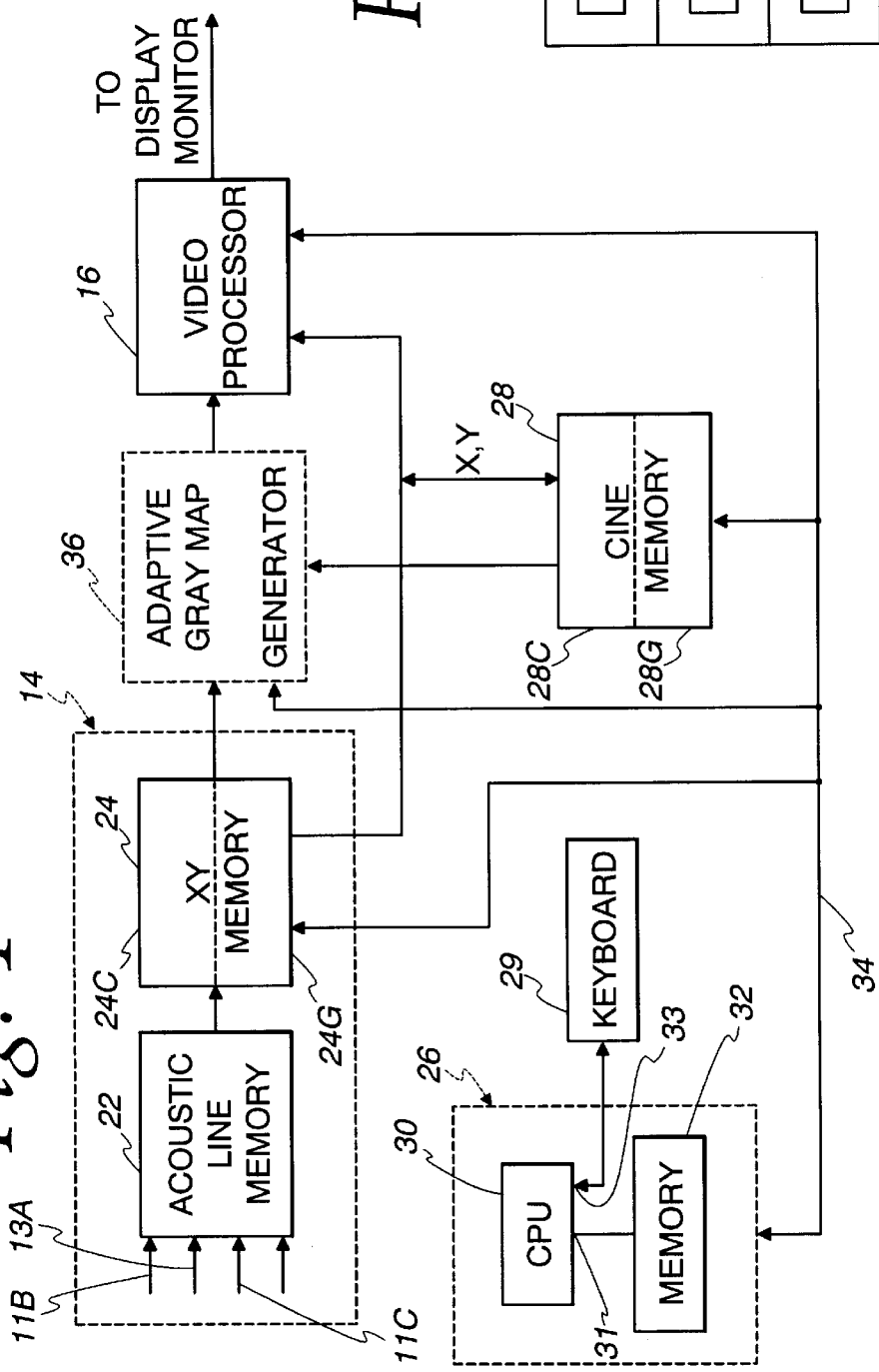
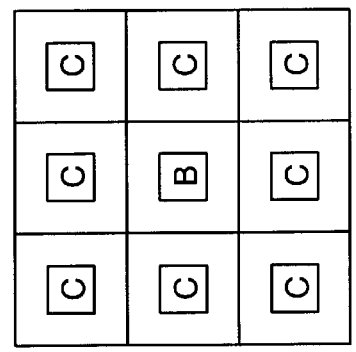

ULTRASOUND COLOR FLOW DISPLAY OPTIMIZATION BY ADJUSTMENT OF THRESHOLD USING SAMPLING

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention generally relates to ultrasound color flow Doppler imaging of fluid flow fields. In particular, the invention relates to a method and an apparatus for improving the display of such imaging.

Ultrasonic scanners for detecting blood flow based on the Doppler effect are well known. Such systems operate by actuating an ultrasonic transducer array to transmit ultrasonic waves into the object and receiving ultrasonic echoes backscattered from the object. In the measurement of blood flow characteristics, returning ultrasonic waves are compared to a frequency reference to determine the frequency shift imparted to the returning waves by flowing scatterers such as blood cells. This frequency, i.e., phase shift, translates into the velocity of the blood flow. The blood velocity is calculated by measuring the phase shift from firing to firing at a specific range gate.

The change or shift in backscattered frequency increases when blood flows toward the transducer and decreases when blood flows away from the transducer. Color flow images are produced by superimposing a color image of the velocity of moving material, such as blood, over a black and white anatomical B-mode image. Typically, color flow mode displays hundreds of adjacent sample volumes simultaneously, all laid over a B-mode image and color-coded to represent each sample volume's velocity.

Typically, color flow processors estimate blood flow velocity, blood flow power, and blood flow variance. Typically, color flow data is used to modify the color of a region of interest on a display screen. The user selects the type of data used for the display. The modes typically available are power only, velocity only or velocity and variance combined.

In current ultrasound scanners, various color flow display parameters are either fixed with no user selectability or are preset to some specific setting and can only be changed if action is taken by the user, one parameter at a time. This limits image quality and user productivity for any given application and scanning situation. There is a need for a scanner in which these same parameters can all be automatically adjusted at the same time to optimize image quality related to color flow display for a specific scanning situation, thus increasing user productivity.

In the color flow power or color flow velocity modes of operation, known ultrasound scanners provide a B/color priority threshold which is user selectable from a softkey menu on the user's console of the scanner. The threshold may be set by the user to various percentages of the maximum B-mode gray scale value. For any pixel within the color mode region of interest (ROI), if the B-mode pixel value exceeds the selected B/color priority threshold, then the B-mode value is displayed for that pixel. Otherwise, the corresponding color pixel value is displayed, if there is one.

However, the actual B-mode data maximum value may vary over a wide range. As a result, the threshold is frequently less than optimal. Accordingly, there is a need for a color flow ultrasound scanner which can automatically adjust the B/color priority threshold according to the actual B-mode data.

BRIEF SUMMARY OF THE INVENTION

This invention is useful in an ultrasound imaging system generating color flow signals in response to ultrasound signals backscattered from a subject under study and generating image signals based on the amplitude of ultrasound signals backscattered from the subject under study. This aspect of the invention displays images in response to the color flow signals by receiving a threshold signal, preferably at a terminal from a memory. A first set of data words is stored in response to the color flow signals, and a second set of data words is stored in response to the image signals, preferably by a digital memory. The threshold signal is adjusted to a first threshold value. Samples of the second set of data words are analyzed to determine an initial count of data words having a first predetermined relationship with respect to the first threshold value, preferably by a logic unit. The threshold signal is adjusted to one or more additional threshold values, preferably by the logic unit. The second data words are sampled one or more additional times until the number of second set data words having the first predetermined relationship with respect to the additional threshold values reaches a target count having a second predetermined relationship with respect to the initial count and corresponding to a target threshold value. Data words are selected from the first and second sets depending on a third predetermined relationship between the target threshold value and the values of the data words in the first and second sets, preferably by the logic unit. A color flow image is displayed in response to the selected data words.

By using the foregoing techniques, the display of an ultrasound imaging system can be automatically adjusted for optimum viewing.

BRIEF DESCRIPTION OF THE DRAWINGS

FIG. 4 is a schematic block diagram showing additional details of portions of the system illustrated in FIG. 1.

FIG. 5 is a schematic illustration of a window illustrating a method of data sampling in accordance with a preferred embodiment of the invention.

DETAILED DESCRIPTION OF THE INVENTION

Figure 1:
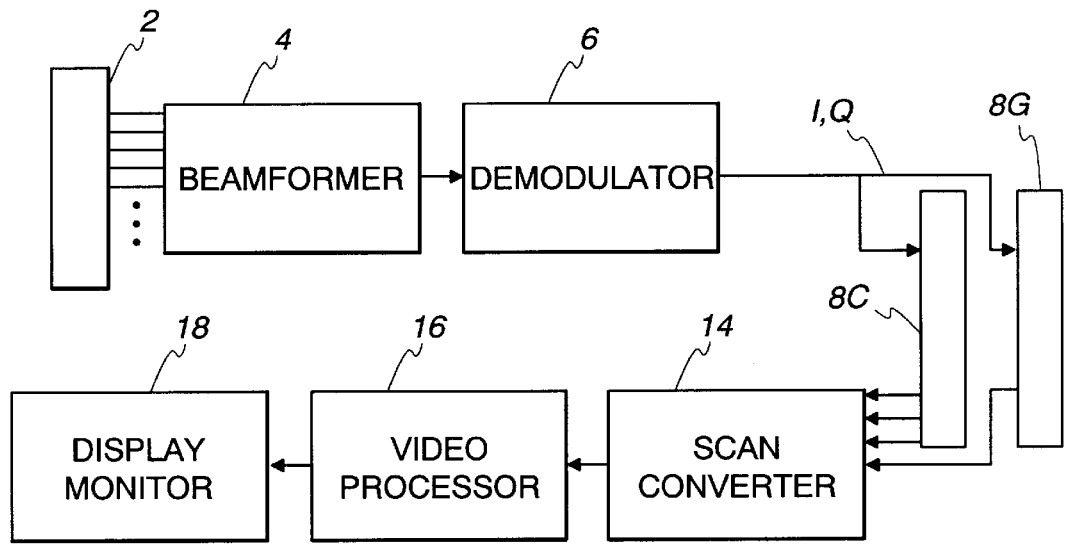
FIG. 1 is a schematic block diagram showing the signal processing chain for a conventional color flow and B-mode ultrasound imaging system.

Referring to FIG. 1, the basic signal processing chain for a color flow and gray scale imaging system comprises an ultrasound transducer array 2, which is activated to transmit pulse sequences comprising tone bursts of length P which are fired repeatedly at a pulse repetition frequency (PRF) which typically is in the kilohertz range. The pulse sequences, including burst lengths P, are different for the color flow and B-mode processing. For color flow imaging, P may be 4 to 8 cycles, and the tone bursts are focused at the same transmit focal position with the same transmit characteristics.

A series of color flow transmit firings focused at the same transmit focal position are referred to as a "packet". Each transmit beam propagates through the object being scanned and is reflected by ultrasound scatterers in the object.

The return RF signals are detected by the transducer elements and received by the respective receive channels in the beamformer 4. The beamformer sums the delayed channel data and outputs in a beam summed signal which is demodulated into in-phase and quadrature (I/Q) signal components by a demodulator 6. The B-mode I, Q outputs from demodulator 6 are transmitted to a mid processor 8G for gray scale B-mode processing, and the color flow I, Q outputs from demodulator 6 are transmitted to a mid-processor 8C for color processing.

Figure 2:
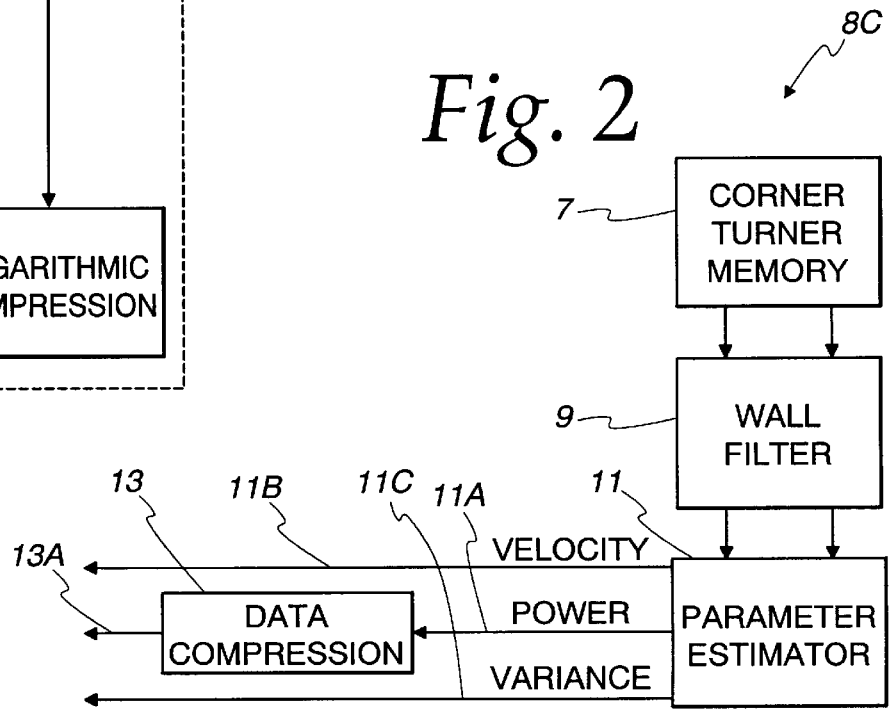
FIG. 2 is a schematic block diagram showing the mid processor color flow apparatus illustrated in FIG. 1.

FIG. 2 illustrates mid-processor 8C. The I/Q signal components from demodulator 6 are stored in a corner turner memory 7, whose purpose is to buffer data from possibly interleaved firings and output the data as vectors of points across firings at a given range cell. Data is received in "fast time", or sequentially down range (along a vector) for each firing. The output of the corner turner memory is reordered into "slow time", or sequentially by firing for each range cell. The resultant "slow time" I/Q signal samples are passed through a wall filter 9 which rejects any clutter corresponding to stationary or very slow-moving tissue. The filtered outputs are then fed into a parameter estimator 11, which converts the range cell information into the intermediate autocorrelation parameters N, D and R(O). N and D are the numerator and denominator for the autocorrelation equation, as shown below:

$$N = \sum_{i=1}^{M-1} (I_i Q_{i+1} - I_{i+1} Q_i) \quad (2)$$

$$D = \sum_{i=1}^{M-1} (I_i I_{i+1} + Q_i Q_{i+1}) \quad (3)$$

where $I_i$ and $Q_i$ are the demodulated, basebanded input data for firing i, and M is the number of firings in the packet. R(O) is approximated as a finite sum over the number of firings in a packet, as follows:

$$R(O) = \sum_{i=1}^{M-1} \frac{(I_i^2 + Q_i^2 + I_{i+1}^2 + Q_{i+1}^2)}{2} \quad (4)$$

A processor converts N and D into a magnitude and phase for each range cell. The equations used are as follows:

$$|R(T)| = \sqrt{N^2 + D^2} \quad (5)$$

$$\phi(R(T)) = \tan^{-1}\left[\frac{N}{D}\right] \quad (6)$$

The parameter estimator processes the magnitude and phase values into signals having values representing estimates of power, velocity and turbulence or variance which are transmitted on conductors 11A, and 11B and 11C, respectively. The phase is used to calculate the mean Doppler frequency, which is proportional to the velocity as shown below; R(O) and |R(T)| (magnitude) are used to estimate the turbulence.

The mean Doppler frequency in hertz is obtained from the phase of N and D and the pulse repetition from T:

$$\bar{f} = \frac{1}{2\pi T}\tan^{-1}\left[\frac{N}{D}\right] = \frac{1}{2\pi T}(\phi(R(T))) \quad (7)$$

The mean velocity is calculated using the Doppler shift equation below. Since θ, the angle between the flow direction and the sampling direction, is not known, cos θ is assumed to be 1.0.

$$\bar{v} = \frac{\bar{f}}{f_o}\frac{c}{2\cos\theta} \quad (8)$$

Preferably, the parameter estimator does not calculate the mean Doppler frequency as an intermediate output, but calculates v directly from the phase output of the processor using a look-up table.

The turbulence may be calculated in the time domain as a second-order series expansion of the variance of the mean Doppler frequency. The time domain expression for turbulence involves calculating the zero-lag and one-lag autocorrelation functions, R(O) and R(T) respectively. The exact autocorrelation functions are approximated by finite sums over the known data in the number of firings in a packet:

$$\sigma^2 = \frac{2}{(2\pi T)^2}\left[1 - \frac{|R(T)|}{R(O)}\right] \quad (9)$$

The mean value signal θ (R(T)) is an estimate of the mean Doppler frequency shift of the flowing reflectors, which in turn is proportional to the mean blood flow velocity. The variance signal $\sigma^2$ indicates the frequency spread of the flow signal component of the baseband echo signal. This value is indicative of flow turbulence, since laminar flow has a very narrow range of velocities, while turbulent flow is a mixture of many velocities. To indicate the strength of the signal from the flowing reflectors, the signal R(O) indicates the amount of the returned power in the Doppler-shifted flow signal.

The signal power on conductor 11A is passed through a data compression module 13 which compresses the data according to families of data compression curves. A different family of curves can be provided for different scanning applications. For example, one family of curves is provided for renal scanning, while another family of curves is provided for carotid artery scanning. Typically, there are about three curves per family. The dynamic range of the signals is changed according to the curve used for the data compression. The curves in each family are arranged in order of increasing dynamic range. Controller 26 sets the default curve when a user selects the scan application. The dynamic range controls the range of intensities or lumens created on display 18.

Figure 3:
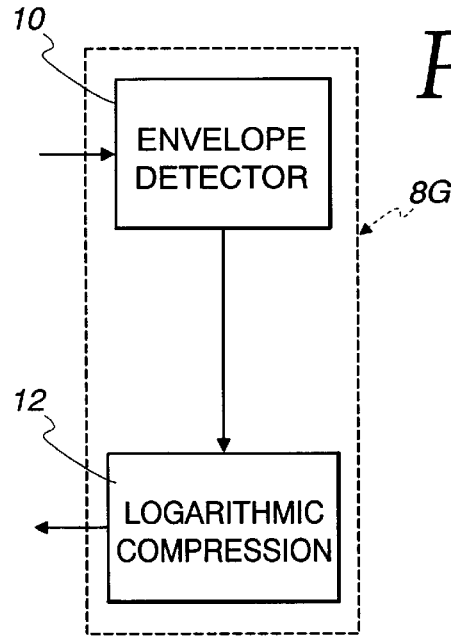
FIG. 3 is a schematic block diagram showing the mid processor B-mode apparatus illustrated in FIG. 1.

Referring to FIG. 3, gray scale B-mode mid-processor 8G includes an envelope detector 10 for forming the envelope of the beamsummed receive signal by computing the quantity $(I^2+Q^2)^{1/2}$. The envelope of the signal undergoes some additional B-mode processing, such as logarithmic compression (block 12 in FIG. 3), to form display data which is output to the scan converter 14 (FIG. 1).

Referring again to FIG. 1, the color flow estimates and gray scale display data are sent to the scan converter 14, which converts the data into X-Y format for video display. The scan-converted frames are passed to a video processor 16, which basically maps the video data to a display color map and gray scale image frames for video display. The image frames are then sent to the video monitor 18 for display. Typically, for color images, either velocity or power are displayed alone or velocity is displayed in conjunction with either power or turbulence. System control is centered in a host computer (not shown), which accepts operator inputs through an operator interface (e.g., a keyboard) and in turn controls the various subsystems.

In general, for B-mode gray scale images, the display data is converted by the scan converter 14 into X-Y format for video display. The scan-converted frames are passed to the video processor 16, which maps the video data to a gray scale or mapping for video display. The gray scale image frames are then sent to the video monitor 18 for display.

The images displayed by the video monitor 18 are produced from an image frame of data in which each datum indicates the intensity or brightness of a respective pixel in the display. An image frame may, e.g., comprise a 256×256 data array in which each intensity datum is an 8-bit binary number that indicates pixel brightness. The brightness of each pixel on the display monitor 18 is continuously refreshed by reading the value of its corresponding element in the data array in a well-known manner. Each pixel has an intensity value which is a function of the backscatter cross section of a respective sample volume in response to interrogating ultrasonic pulses and the gray map employed.

Referring to FIG. 4, system control is centered in a master controller or host computer 26, which accepts operator inputs through an operator interface (not shown) and in turn controls the various subsystems. The master controller 26 also generates the system timing and control signals. The master controller 26 comprises a central processing unit (CPU) 30 and a random access memory 32. A keyboard 29 is used to enter data into CPU 30. The CPU 30 has read only memory incorporated therein for storing routines used in constructing gray and color maps based on acquired raw data.

The scan converter 14 comprises an acoustic line memory 22 and an X-Y memory 24. The B-mode and color mode intensity data stored in polar coordinate (R-θ) sector format in acoustic line memory 22 is transformed to appropriately scaled Cartesian coordinate pixel display data, which is stored in X-Y memory 24. The color data is stored in memory locations 24C, and the gray scale data is stored in memory locations 24G. The scan-converted frames are passed to video processor 16, which maps the data to a gray map for video display. The gray scale image frames are then sent to the video monitor for display.

Successive frames of acoustic sample data are stored in cine memory 28 on a first-in, first-out basis. Color frames are stored in memory locations 28C, and gray scale frames are stored in memory locations 28G. In the color region of interest, for every word of color data corresponding to a display pixel, there is a corresponding word of B-mode gray scale data corresponding to that pixel. The cine memory is like a circular image buffer that runs in the background, continually capturing acoustic sample data that is displayed in real time to the user. When the user freezes the system, the user has the capability to view acoustic sample data previously captured in cine memory.

The CPU 30 controls the XY memory 24 and the cine memory 28 via the system control bus 34. In particular, the CPU 30 controls the flow of raw data from the XY memory 24 to the video processor 16 and to the cine memory 28 and from the cine memory to the video processor 16 and to the CPU 26 itself. The CPU also loads the gray maps and color maps into the video processor.

Image frames are collected in cine memory 28 on a continuous basis. The cine memory 28 provides resident digital image storage for single image review and multiple image loop review and various control functions. The region of interest displayed during single-image cine replay is that used during the image's acquisition. The cine memory also acts as a buffer for transfer of images to digital archival devices (not shown) via the master controller 26.

The CPU 30 has random access memory for storing routines used in acquiring a raw data histogram, determining the end points of a new gray map input range, constructing a new gray map based on the end points of the new gray map input range, comparing the slope and gain of the new gray map to predetermined slope and gain limits, and if either limit is exceeded, reconstructing the new gray map to conform to the limit or limits.

In accordance with the preferred embodiments of the invention, the contrast of the ultrasound images is adjusted by the master controller 26 by creating a mapping of raw acoustic sample data into adjusted gray and color map values. First, the master controller 26 retrieves one or more image frames of raw data from the X-Y memory 24 or from the cine memory 28, storing that raw data in memory 32. The CPU 30 then compiles a histogram of the number of acoustic samples having an amplitude or value within each of a multiplicity of prescribed ranges or bins for the retrieved image frames of raw data.

According to the preferred embodiment, a color flow auto display processing mode is initiated by the user through keyboard 29 (FIG. 4) and can then be re-initiated by the user for updating of post-processing parameters or turned off altogether as the scanning situation changes.

The preferred embodiment uses the above-described B-mode gray scale and color flow scan data to optimize image quality of the color display. A composite histogram (histogram of the data over several frames) and/or a single frame histogram are constructed from the cine memory 28 data for color flow and/or B-mode by controller 26. Algorithms then are applied to the histogram results by controller 26 to determine how to properly adjust various parameters for a specific scanning situation or application.

The Algorithms are Described as Follows

By operating keyboard 29, the user may enter the color flow modes in which power and velocity data are used separately. In those modes, there is a B/color priority threshold which is user selectable from a softkey menu on keyboard 29 and which is preset to x% of the maximum B-mode gray scale value of 255. The threshold is received, for example, at terminals 31 and 33. For any pixel within the color mode region of interest (ROI), if the B-mode pixel value exceeds the selected B/color priority threshold, then the B-mode value is displayed for that pixel. Otherwise, the corresponding color pixel value is displayed, if there is one.

The algorithm captures N frames of B-mode data from cine memory 28G in the color ROI and N frames of color flow velocity or power data from cine memory 28C in the color ROI (depending on which mode the user is in). The number of nonzero occurrences of color flow pixels in each frame in the ROI is calculated. Then a single frame of color flow data along with its corresponding B-frame of data is selected from the N frames based on which color frame has the most total number of occurrences of color flow (nonzero) pixel data. The single B-frame of data and single color frame of data are then analyzed as follows:

An m-pixel by m-pixel filter is applied across the B/color 2-dimensional ROI data array formed by the frame of B-mode and frame of color mode data to determine the baseline number of B-mode "holes" in the image with an effective B/Color priority threshold of 100% applied. For example, a 3-pixel by 3-pixel filter would look for a single B pixel value surrounded by all color pixel values with the B/color priority threshold set to 100%. The threshold preferably is applied only to the B pixel value. This filter would be applied across the entire 2-dimensional ROI data and a single filtered result would appear as shown in FIG. 5 when a B-mode "hole" is present in the color flow data array.

When this filter is applied across the entire B mode and color data arrays using a B/color priority threshold of 100%, an initial or baseline count of the number of B-mode "holes" is established. Since the threshold is 100%, the baseline count is a minimum count. Then the B/color priority threshold is incrementally lowered, and the filter is again applied each time for each new B/color priority threshold, establishing a new count of the B-mode "holes". This process of lowering the threshold and of establishing a new count is continued until the number of B-mode "holes" is some factor k greater than the minimum number of baseline B-mode "holes" in the baseline count. Factor k is preset differently as the user selects tissue type and flow type via keyboard 29. Preferably, the baseline count at the 100% threshold is equal to or greater than 1. The factor k can be an offset or a multiple of the baseline count. Then this final B/color priority threshold is used to continue imaging. This process happens quickly enough that there is essentially no significant delay to the user. The threshold is used to create an image on display 18 in the manner previously described.

At any time, the user can cause new data to be captured and the algorithm to be re-employed. Such reactivation is useful for new scanning conditions. Or the user can turn off the algorithm, causing the current B/color priority threshold to be maintained until the user manually changes the setting.

The embodiments described here can be extended to automatically adjust other post-processing parameters such as power thresholds, wall filter cutoffs, baseline shifts, and velocity scales. The same basic idea of collecting B and/or color flow frames of cine data would be applied and associated algorithms would be employed to determine exactly how to adjust the particular post processing parameter.

The foregoing preferred embodiments have been disclosed for the purpose of illustration. Variations and modifications of the concept of the invention will be readily apparent to persons skilled in the art. All such variations and modifications are intended to be encompassed by the claims set forth hereinafter.

What is claimed is:

1. In an ultrasound imaging system generating color flow signals in response to ultrasound signals backscattered from a subject under study and generating image signals based on the amplitude of ultrasound signals backscattered from the subject under study, improved apparatus for displaying images in response to the color flow signals comprising in combination:

a terminal connected to receive a threshold signal;

a memory connected to store a first set of data words in response to the color flow signals and a corresponding second set of data words in response to the image signals;

a logic unit connected to adjust the threshold signal to a first threshold value, to analyze samples of the second set of data words to determine an initial count of data words having a first predetermined relationship with respect to the first threshold value, to adjust the threshold signal to one or more additional threshold values and to analyze samples of the second data words one or more additional times until the number of second set data words having the first predetermined relationship with respect to the additional threshold values reaches a target count having a second predetermined relationship with respect to the initial count and corresponding to a target threshold value, and to select data words from the first and second sets depending on a third predetermined relationship between the target threshold value and the values of the data words in the first and second sets; and a display connected to display a color flow image in response to the selected data words.

2. Apparatus, as claimed in claim 1, wherein the image signals comprise B-mode signals.

3. Apparatus, as claimed in claim 1, wherein the color flow signals comprise power signals representing power estimates calculated in response to the backscattered signals.

4. Apparatus, as claimed in claim 1, wherein the color flow signals comprise velocity signals representing velocity estimates calculated in response to the backscattered signals.

5. Apparatus, as claimed in claim 1, wherein the additional threshold values are less than the first threshold value.

6. Apparatus, as claimed in claim 1, wherein each of the samples comprises one or more data words from the second set having a fourth predetermined relationship with respect to corresponding data words from the first set.

7. Apparatus, as claimed in claim 6, wherein the fourth predetermined relationship comprises one or more words from the second set which when displayed are surrounded by images resulting from data words from the first set.

8. Apparatus, as claimed in claim 1, wherein the first predetermined relationship comprises data words having values exceeding the first threshold value.

9. Apparatus, as claimed in claim 1, wherein the second predetermined relationship comprises a target count which is a multiple of the initial count.

10. Apparatus, as claimed in claim 1, wherein the third predetermined relationship comprises selection of a data word in the second set if the value of the data word in the second set compares to the target threshold value in a predetermined manner and selection of a data word in the first set if the value of the data word in the second set fails to compare to the target threshold value in the predetermined manner.

11. Apparatus, as claimed in claim 1, wherein the terminal comprises an input operable by a user.

12. In an ultrasound imaging system generating color flow signals in response to ultrasound signals backscattered from a subject under study and generating image signals based on the amplitude of ultrasound signals backscattered from the subject under study, an improved method for displaying images in response to the color flow signals comprising the steps of:

receiving a threshold signal;

storing a first set of data words in response to the color flow signals and a second set of data words in response to the image signals;

adjusting the threshold signal to a first threshold value;

analyzing samples of the second set of data words to determine an initial count of data words having a first predetermined relationship with respect to the first threshold value;

adjusting the threshold signal to one or more additional threshold values;

analyzing samples of the second data words one or more additional times until the number of second set data words having the first predetermined relationship with respect to the additional threshold values reaches a target count having a second predetermined relationship with respect to the initial count and corresponding to a target threshold value;

selecting data words from the first and second sets depending on a third predetermined relationship between the target threshold value and the values of the data words in the first and second sets; and displaying a color flow image in response to the selected data words.

13. A method, as claimed in claim 12, wherein the image signals comprise B-mode signals.

14. A method, as claimed in claim 12, wherein the color flow signals comprise power signals representing power estimates calculated in response to the backscattered signals.

15. A method, as claimed in claim 12, wherein the color flow signals comprise velocity signals representing velocity estimates calculated in response to the backscattered signals.

16. A method, as claimed in claim 12, wherein the additional threshold values are less than the first threshold value.

17. A method, as claimed in claim 12, wherein each of the samples comprises one or more data words from the second set having a fourth predetermined relationship with respect to corresponding data words from the first set.

18. A method, as claimed in claim 17, wherein the fourth predetermined relationship comprises one or more words from the second set which when displayed are surrounded by images resulting from data words from the first set.

19. A method, as claimed in claim 12, wherein the first predetermined relationship comprises data words having values exceeding the first threshold value.

20. A method, as claimed in claim 12, wherein the second predetermined relationship comprises a target count which is a multiple of the initial count.

21. A method, as claimed in claim 12, wherein the step of selecting data words comprises the step of selecting a data word in the second set if the value of the data word in the second set compares to the target threshold value in a predetermined manner and selecting a data word in the first set if the value of the data word in the second set fails to compare to the target threshold value in the predetermined manner.

22. A method, as claimed in claim 12, wherein the step of receiving comprises the step of generating a threshold signal based on user input.

* * * * *